(12) United States Patent
Spaargaren et al.

(10) Patent No.: US 9,022,212 B2
(45) Date of Patent: May 5, 2015

(54) ELONGATED ENDOLUMINAL DEVICE PACKAGING SYSTEM AND METHOD

(71) Applicant: Volcano Corporation, San Diego, CA (US)

(72) Inventors: Kevin Spaargaren, Winchester, CA (US); Aaron Guerrero, San Luis Obispo, CA (US); Katie Keller, San Diego, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 13/753,586

(22) Filed: Jan. 30, 2013

(65) Prior Publication Data
US 2013/0206623 A1 Aug. 15, 2013

Related U.S. Application Data

(60) Provisional application No. 61/592,459, filed on Jan. 30, 2012.

(51) Int. Cl.
*A61M 25/00* (2006.01)
*A61B 19/02* (2006.01)

(52) U.S. Cl.
CPC ............ *A61B 19/026* (2013.01); *A61M 25/002* (2013.01); *A61B 19/0271* (2013.01); *A61B 2019/0209* (2013.01); *A61B 2019/0278* (2013.01)

(58) Field of Classification Search
USPC ......... 206/364, 363, 438, 570, 571, 370, 560, 206/701, 702, 726, 728, 565, 564, 389, 206/63.3, 303; 600/585; 604/171; 242/172; 7/364, 363, 438, 570, 571, 370, 560, 7/701, 702, 726, 728, 565, 564
See application file for complete search history.

(56) References Cited

U.S. PATENT DOCUMENTS

| | | | | |
|---|---|---|---|---|
| 3,851,649 | A * | 12/1974 | Villari | 206/438 |
| 5,344,011 | A * | 9/1994 | DiBernardo et al. | 206/364 |
| 5,947,284 | A * | 9/1999 | Foster | 206/364 |
| 6,053,313 | A * | 4/2000 | Farrell et al. | 206/364 |
| 7,401,703 | B2 * | 7/2008 | McMichael et al. | 206/570 |
| 7,491,176 | B2 * | 2/2009 | Mann | 600/564 |
| 7,815,045 | B2 * | 10/2010 | Delaney et al. | 206/364 |

(Continued)

FOREIGN PATENT DOCUMENTS

WO WO/2004026383 4/2004

OTHER PUBLICATIONS

International Searching Authority/KIPO, "Notification of Transmittal of the International Search Report and the Written Opinion of the International Searching Authority, or the Declaration," for PCT/US2013/023787, mailed Jun. 13, 2013,11 pages.

*Primary Examiner* — Mickey Yu
*Assistant Examiner* — Allan Stevens
(74) *Attorney, Agent, or Firm* — Haynes and Boone, LLP (57) ABSTRACT

A package system and method are provided for storing and shipping of elongated endoluminal devices. In one aspect, the system includes a packaging tray having a first area to maintain the position of a first portion of the elongated endoluminal device and a second portion retaining an opposing portion of the elongate device. The second portion configured to hold the coupling element of the assembly and being radially spaced outward from the first portion.

9 Claims, 7 Drawing Sheets

(56) References Cited

U.S. PATENT DOCUMENTS

| | | |
|---|---|---|
| 7,886,906 B1 | 2/2011 | Dunn |
| 2002/0130059 A1 | 9/2002 | Armijo |
| 2007/0193903 A1 | 8/2007 | Opie et al. |
| 2009/0065034 A1 | 3/2009 | Suzuki et al. |
| 2009/0177090 A1* | 7/2009 | Grunwald et al. ............ 600/454 |

* cited by examiner

ELONGATED ENDOLUMINAL DEVICE PACKAGING SYSTEM AND METHOD

The present application claims priority to and the benefit of U.S. Provisional Patent Application No. 61/592,459, filed Jan. 30, 2012, which is hereby incorporated by reference in its entirety.

FIELD OF THE INVENTION

The present invention is directed to a holder for retaining an elongated endoluminal device such as a guide wire or catheter. More specifically, the invention is directed to a support tray for retaining an elongated endoluminal device within a package, the support tray is useful for securing the device during shipping, storage, and prior to use on a patient.

BACKGROUND OF THE INVENTION

Elongated endoluminal devices, such as guide wires and catheters are tubular medical devices for insertion into canals, vessels, passageways, or body cavities; often to permit the injection or withdrawal of fluid, to keep a passage open, to take internal measurements, image the vessel from the interior, deliver energy to treat the vessel, among many possible uses. While catheters and guide wires vary in size, shape, and function, they frequently consist of a very long, flexible, and thin tubular portion connected to a more rigid proximal portion. The tubular portion may be a meter or longer in length, and only a fraction of an inch in diameter. The head may be, for example, an inch or two in length and a fraction of an inch in diameter.

The tubular portion of the catheter is usually hollow, and may have one or more lumens running along its entire length. The lumen or lumens function as a way of inserting various devices into the catheter. For example, catheters frequently travel along a guide wire running through one of the lumens. Alternatively, the lumens may receive mechanical devices, control wires, electrical connectors or wires, optical fibers or other devices for assisting in diagnostic, therapeutic or surgical operations.

Due to the extremely fine and often delicate nature of the lumens and electrical connections, as well as the tight tolerances associated with many of the applications to which devices are applied, devices must necessarily be handled, stored, and shipped with great care. Mechanical or chemical abrasion to any portion of the exterior of the device can cause problems to the subsequent use of the device. Also, deformation of the device can be a problem if it results in leaving the device damaged or transformed in any way. Thus, significant bending of the device should normally be avoided during the storage of a device to avoid any "memory" of the bend, pinched lumens, or broken electrical connections. Such binding should also be avoided while installing or removing a device from a storage or shipping package.

Figure 1:
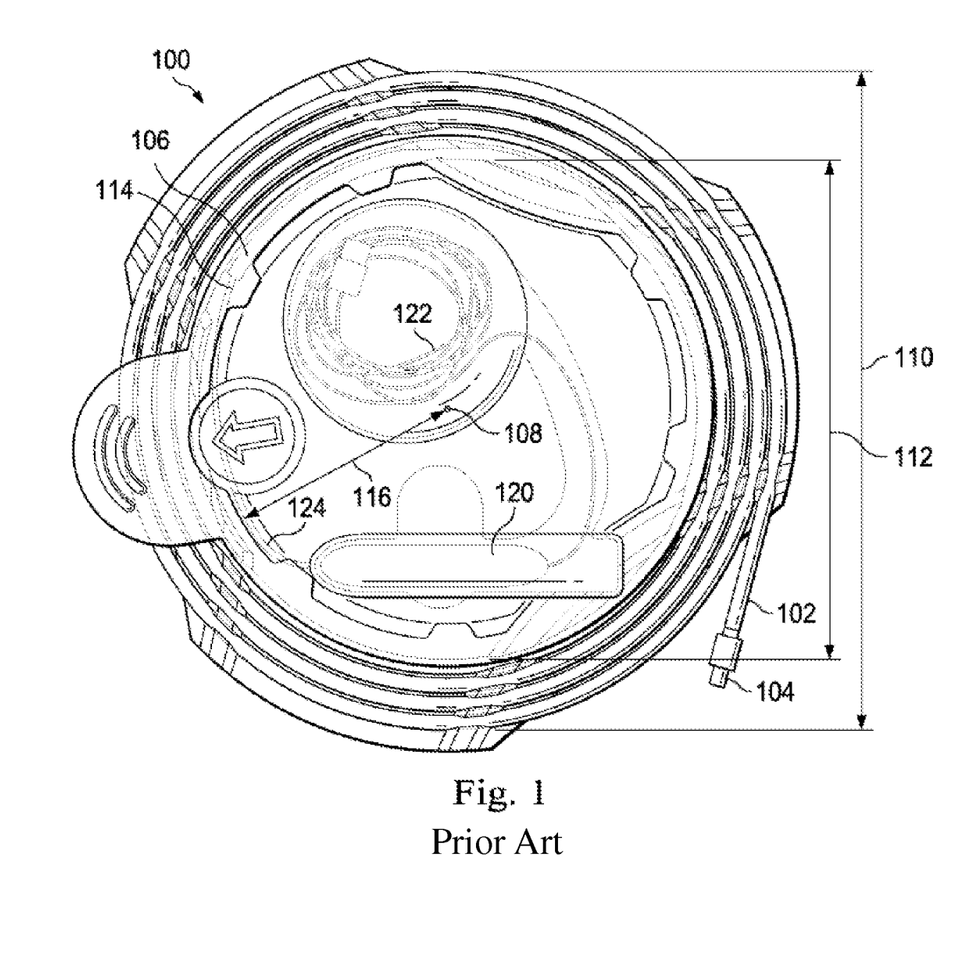
FIG. 1 is a top view of a prior packaging system.
Figure 2:
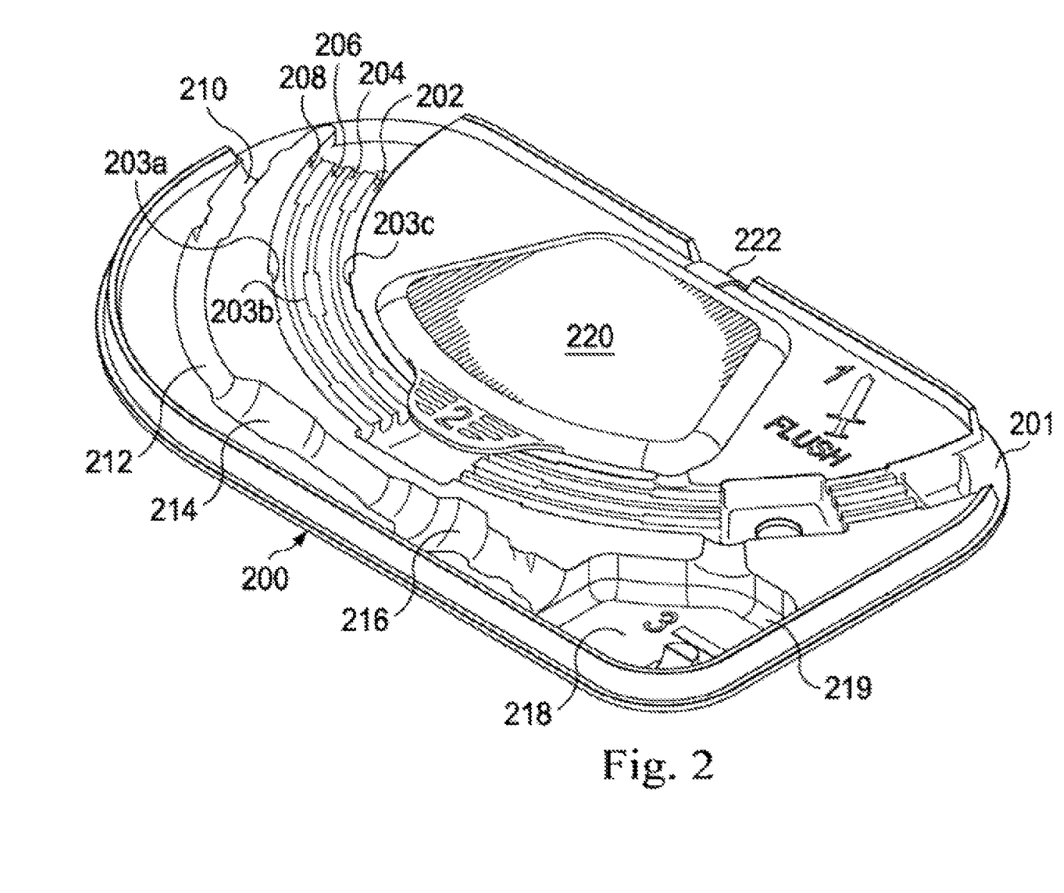
FIG. 2 is a perspective view of a support tray according to one embodiment of the present disclosure.
Figure 3:
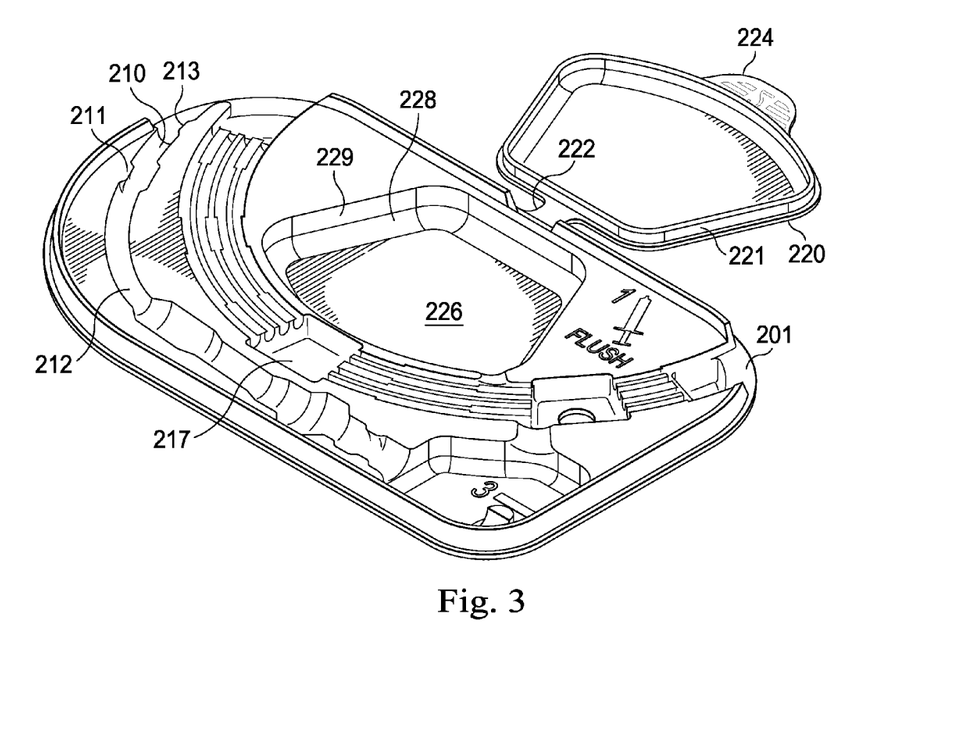
FIG. 3 is an alternative perspective view of the support tray of FIG. 2.

Referring now to FIG. 1, there is shown an existing packaging system 100. Protective sheath tubing 102 is wound in a spiral fashion around center 108. A luer lock 104 is positioned on the outermost termination and can be used for flushing the tubing 102. The spiral tubing has an outer radius 110 of approximately 4.5 inches, with an outer diameter of approximately 9 inches, and spirals inward to an inner radius 112 of approximately 3.6 inches at inner most termination 106. A pressure sensing guide wire 114 is disposed within the tubing 102 and exits at termination 106. The pressure wire 114 continues inward sharply to the entry of coupler 120 disposed at a radius 116 of approximately 3.2 inches. Given the short distance between the termination 106 of tube 102 and the connector 120, the wire experiences a sharp bending radius of approximately 1.75 inches adjacent curve 124 which is adjacent electrical connectors disposed within the connector 120.

Unfortunately, for some types of devices, such as sensitive pressure wires, positioning during packaging and handling during shipping cause damage to the guide wire and/or the associated electrical connections. As a result, the pressure wires are inoperable or inaccurate when an attempt is made to introduce them into the patient on the operating or catheter lab table.

Thus, there remains a need for packaging systems and techniques that can limit damage to delicate elongated endovascular devices. The devices, systems, and methods disclosed herein overcome one or more of the deficiencies of the prior art.

SUMMARY

In one aspect, the present disclosure provides an elongated endoluminal device package system for receiving an elongated endovascular device having at least one component located adjacent a distal end and at least one connector located adjacent a proximal end. The system provides a first retention area for maintaining the elongated endoluminal device in a first spiral radius configuration, a second retention area for maintaining coupling components of the system that are connected to the elongated device, and a transition area where the wire transitions from the spiral configuration to the coupling components while maintaining a radius of curvature of the elongate device equal to or greater than the radius of curvature of the elongated device in the spiral configuration. In one aspect, the elongated device is a sensing guide wire. In a further aspect, the elongated device is a pressure sensing guide wire.

The present disclosure further includes a method of packing an elongated endoluminal device in a package system to maintain it in a position as set forth above. In one aspect, the endoluminal device is a an endovascular pressure sensing guide wire.

Still further, the present disclosure provides a kit having a guide wire maintained in a protected condition. In one aspect, the protected condition of the kit includes limiting the radius of curvature of the elongated member to be not less than the radius of the inner most coil of the protective sheath surrounding the elongate member.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and referenced by the same reference number. The characteristics, attributes, functions, interrelations ascribed to a particular element in one location apply to those elements when referred to by the same reference number in another location unless specifically stated otherwise.

The figures referenced below are drawn for ease of explanation of the basic teachings of the present disclosure only; the extensions of the figures with respect to number, position, relationship and dimensions of the parts to form the preferred embodiment will be explained or will be within the skill of the art after the following description has been read and understood. Further, the exact dimensions and dimensional proportions to conform to specific force, weight, strength and similar requirements will likewise be within the skill of the art after the following description has been read and understood.

The following is a brief description of each figure used to describe the present invention, and thus, is being presented for illustrative purposes only and should not be limitative of the scope of the present invention.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

Figure 7:
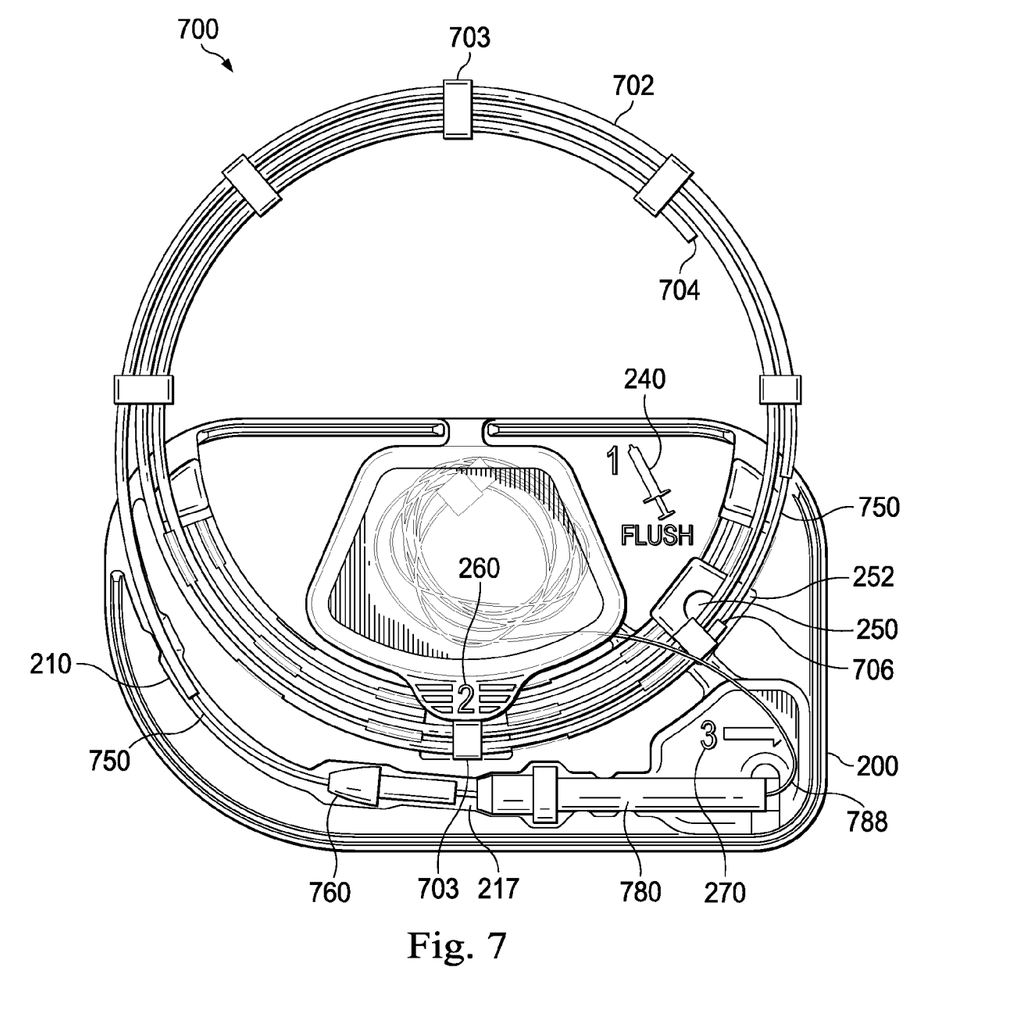
FIG. 7 is a top view of a package system kit according to one embodiment of the present disclosure.

Referring now to FIGS. 2-6, there is illustrated a package support tray 200. The support tray is formed of a rigid body having a series of spiraling channels 202, 204, 206 and 208 extending outwardly in increasing radii from center point 288. The innermost spiral channel 202 has an inner radius 290 of approximately 3.91 inches. The channel radius expands to outer channel 208 having an outer radius 292 of approximately 4.56 inches. A protective tube terminus mounting 210 is provided within terminal channel 212. Terminus mount 210 includes at least two flanges 211 and 213 that removably retain a protective tube 702, such as shown in FIG. 7, within the channel 210. Torque device cavity 214 extends from channel 212 and leads into connector cavity 216. The end of channel 212 is positioned approximately 5 inches from center 288 along radius 294.

Figure 4:
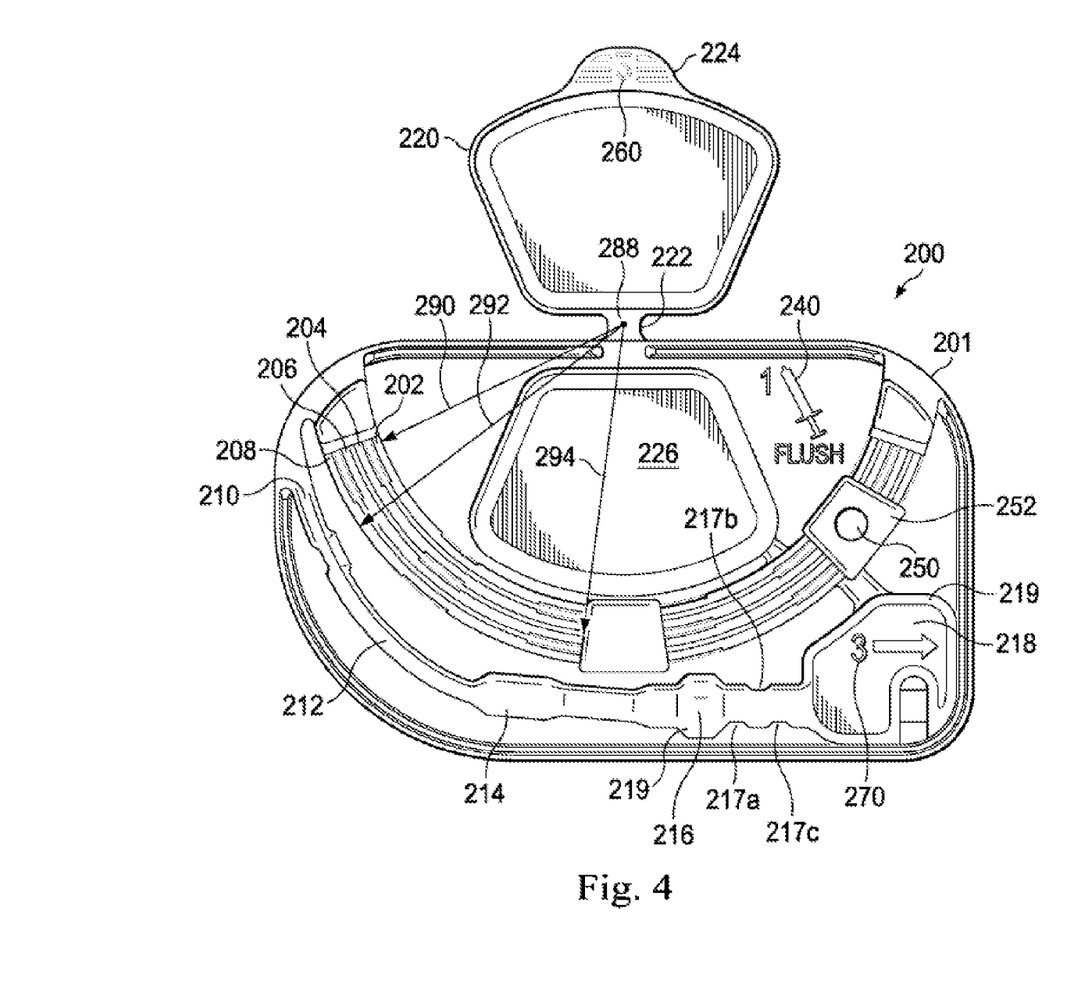
FIG. 4 is a top view of the support tray of FIG. 2.
Figure 5:
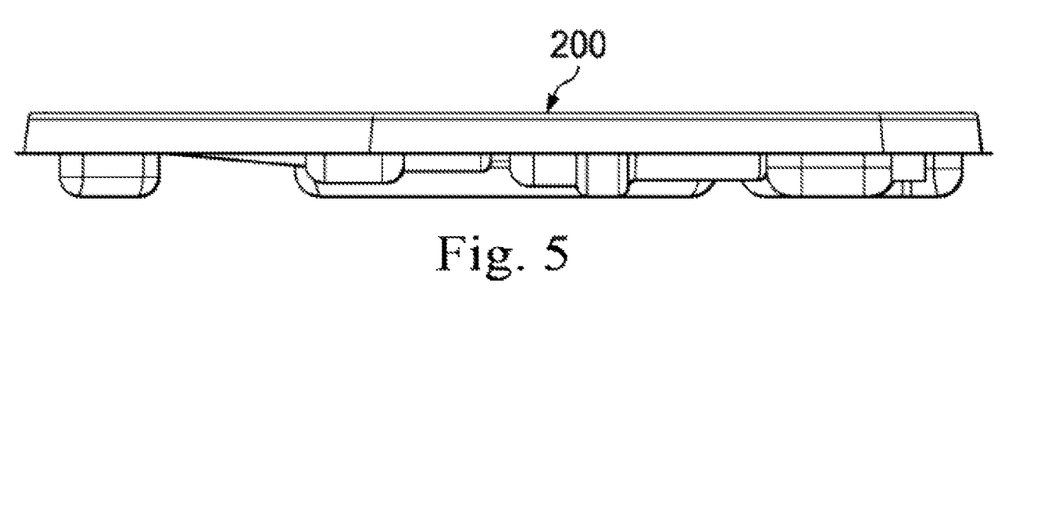
FIG. 5 is a bottom view of the support tray of FIG. 4.
Figure 6:
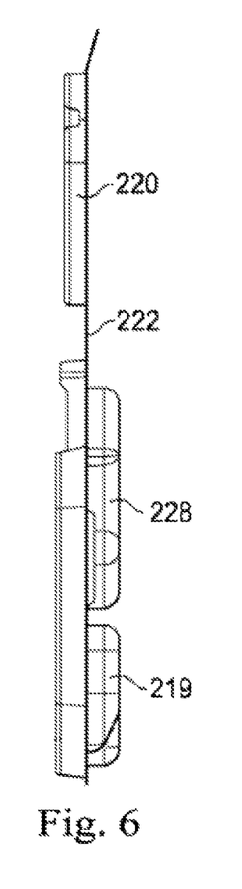
FIG. 6 is a side view of the support tray of FIG. 4

As shown in FIG. 7, the torque device cavity 214 receives the torque device 760 and the connector cavity 216 is sized to receive the connector 780. Referring now to FIG. 4, the connector cavity includes an enlarged annular ring 219 and a series of flexible flanges 217a, 217b and 217c configured releasably secure the connector in the connector cavity 216. Together with the side walls forming the cavity 216, the annular ring 219 and flanges 217 form an interference connection to prevent the connector 780 from moving with respect to the support tray 200 until released by the user. In contrast, the torque device cavity 214 loosely holds the torque device such that when connector 780 is removed from cavity 216, the torque device may freely leave cavity 214. In this manner, the packaging system support tray 200 avoids unnecessary stress or bending of the guide wire as the user frees the torque device from the tray.

Lid 220 is joined to the main body 201 by a flexible flange 222 and has an outer annular side wall 221. Lid 220 is sized to cover compartment 226 defined by circumferentially extending lower side walls 228 and upper side wall 229. The outer side wall 221 of the lid engages the inner side wall 229 of the recess to form an interference fit that retains the lid in the closed position. Lid 220 includes a tab 224 that can be grasped by a user to overcome the force of the interference fit to thereby open the lid. The lid also includes an indicator "2" as shown by reference number 260 in FIGS. 4 and 7.

Referring now to FIG. 7, there is shown a pre-packaged kit 700 including the support tray 200, protective tubing 702, guide wire 750, torque device 760, wire connector 780, and signal cable 788. In comparison to the packaging of FIG. 1, the support tray 200 is about one half the size, thus requiring less material to manufacture the support tray. The steps for packaging include positioning the guide wire 750 within the protective tubing 702 with the distal most end of the guide wire positioned proximate distal tube end 704. As shown in FIG. 7, tubing 702 includes two tubing sections spaced from one another by gap 706. The tubing 702 is then spiral coiled into the configuration shown in FIG. 7 with clips 703 maintaining the spacing between adjacent coils. The coil assembly is then positioned in the support tray 702 with the tubing 702 extending in as many channels 202-208 as necessary. During mounting onto the support tray, the gap 706 in the tubing is positioned over reservoir 250 and lower clip 703 is positioned in recess 217. The illustrated wire is approximately 185 cm in length and uses two channels, while a 300 cm long wire would use all four channels. The guide wire is in the range of 0.018 to 0.010 inches in diameter with the illustrated wire having a diameter of typical 0.0145 inches. The proximal end of the pressure sensing wire 750 is positioned through the torque device 760 and into an electrical connector device 780. In the illustrated embodiment, the coupling device has a lock mechanism that is moved to the locked position to firmly hold the wire 750 within the connector during shipping. The connector 780 includes a signal cable 788 for connection to a system interface module that is positioned in cavity 226 with lid 220 closed for shipping.

With the pressure wire 750 positioned in the components, the tubing 720 is pushed into channels 202-208 past the series of flexible flanges 203a, 203b and 203c that extend along the channels to releasably hold the tubing in the channels. As best seen in FIG. 4, the tray includes a series of flexible flanges similar to flanges 203 alternating between two and three flanges as the channels extend from one side of the tray to the opposite side of the tray. The terminal end is positioned in terminus mount 210 which includes at least flanges 211 and 213 that removably retain tube 702. Similarly, torque device 760 is positioned in cavity 214 and connector 780 is pushed past flanges 217a, 217b and 217c to be releasably retained in cavity 216 with the enlarged locking mechanism ring positioned in annular groove 219. The excess cord of the signal cable 788 is positioned in cavity 226 and lid 220 is closed to retain the cable in position during shipping.

The support tray 200 permits the device to be spirally wound and supported with the exposed proximal portion of the wire extending to the coupler undergoing a radius of curvature that is greater than the more centrally or interior windings of the wire. Thus, the wire is maintained in a lower bending stress position during shipping, particularly those components near the sensitive elements of the proximal end of the pressure wire.

As shown in FIG. 7, the tray has a position for the wire and connected coupler that is disposed radially outward from the central point 288 a distance that is greater than the radial distance of the inner most or outer most winding of the spirally wound protective tubing. Thus, the system of FIG. 7 provides a protective package and guide wire kit that is ready for use when unpacked adjacent a patient.

When unpacking the kit of FIG. 7, the user is directed to follow the steps "1", "2" and "3" engraved on the support tray 200. Step "1" shown at reference number 240, is to connect a syringe to the distal end 704 of tubing (which may be provided with a luer lock, not shown) to flush the distal portion of the tubing and sensing components at the distal end of the guide wire. The flushing fluid exits the tubing 702 at gap 706 and enters reservoir 252 which has a drain opening 250. In this manner, the fluid can be captured and prevented from accidently getting onto other components. More specifically, the tray 200 has been designed to keep fluids used during the flushing procedure away from the connector 780 open end receiving the guide wire as the electrical connections between the guide wire and connector may be adversely effected by fluid. In another design feature, reservoir 218 is recessed below the lower most portion of connector cavity 216 to drain any fluid that may inadvertently enter cavity 216.

After completing step 1, the engraving step "2" at reference 260 directs the user to open lid 220. The user can then withdraw signal cable 788 and connect the connector to a patient interface module to check the sensor and make any calibrations. After step "2" is completed, the user proceeds to step "3" at reference number 270. The user must vertically remove the connector 780 and the direction of the arrow shown at step "3" directs the user how to remove connector 780 along with the torque device 760. The user continues to move the connector 780 in the direction of the arrow to withdraw the pressure sensing guide wire from the protective tubing 702 until the entire wire is exposed. At this point the user may now use the guide wire.

It will be understood that the support tray and package system can be utilized with a variety of sensing guide wires, catheters or other elongated medical devices. In addition, the package systems can also support therapeutic devices including angioplasty balloon devices, arthectomy devices and other elongated flexible devices.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An elongated endoluminal device package system for receiving an elongated endoluminal device having at least one component located adjacent a distal end and at least one connector located adjacent a proximal end, the system comprising:
   a support tray having a first retention area including a plurality of channels for maintaining the elongated endoluminal device in a spiral configuration, a second retention area for maintaining the at least one connector, and a transition area where the elongated endoluminal device transitions from the spiral configuration to the at least one connector;
   wherein a radius of curvature of the transition area is equal to or greater than a radius of curvature of the plurality of channels;
   wherein the support tray further includes a third retention area for maintaining a torque device coupled to the elongated endoluminal device and a reservoir having a drain opening configured to receive fluid using during a flushing procedure;
   wherein the first retention area includes a plurality of flanges configured to releasably secure the elongated endoluminal device within the plurality of channels, the second retention area includes a plurality of flanges configured to releasably secure the at least one connector within the second retention area, and the transition area includes a plurality of flanges configured to releasably secure the elongated endoluminal device within the transition area; and
   wherein first and second flexible support tubes are capable of receiving portions of the elongated endoluminal device, the first and second flexible support tubes spaced from each other such that a gap extending therebetween is positioned proximate to the reservoir of the support tray.

2. The system of claim 1, further including a closable compartment defined adjacent the plurality of channels.

3. A kit, comprising:
   an elongated endoluminal device having a distal end and a proximal end, at least one connector being located adjacent the proximal end;
   a flexible support tube receiving the elongated endoluminal device therein;
   a support tray having a first retention area including a plurality of channels for maintaining the flexible support tube containing the elongated endoluminal device in a spiral configuration, a second retention area for maintaining the at least one connector, and a transition area where the elongated endoluminal device transitions from the spiral configuration to the at least one connector;
   wherein the transition area maintains a radius of curvature for the elongated endoluminal device equal to or greater than a radius of curvature of the elongated endoluminal device in the spiral configuration; and
   wherein the support tray further includes a third retention area for maintaining a torque device coupled to the elongated endoluminal device
   a further flexible support tube, wherein portions of the elongated endoluminal device are received in the flexible support tube and the further flexible support tube, and wherein the flexible support tube and the further flexible support tube are positioned with a gap extending therebetween;
   wherein the support tray further includes a reservoir having a drain opening configured to receive fluid used during a flushing procedure, and wherein the flexible support tube and the further flexible support tube are positioned such that the gap extending therebetween is positioned proximate to the reservoir.

4. The kit of claim 3, wherein the support tray further includes a closable compartment defined adjacent the plurality of channels.

5. The kit of claim 3, wherein the third retention area is positioned between the transition area and the second retention area.

6. The kit of claim 3, wherein the third retention area is sized and shaped to loosely maintain the torque device within the third retention area.

7. The kit of claim 3, wherein:
- the first retention area includes a flange configured to releasably secure the flexible support tube within the plurality of channels;
- the second retention area includes a flange configured to releasably secure the at least one connector within the second retention area; and
- the transition area includes a flange configured to releasably secure the flexible support tube within the transition area.

8. The kit of claim 3, wherein the elongated endoluminal device is an endovascular pressure sensing guidewire.

9. The system of claim 1, wherein the third retention area is positioned between the transition area and the second retention area.

* * * * *